Figure 1:
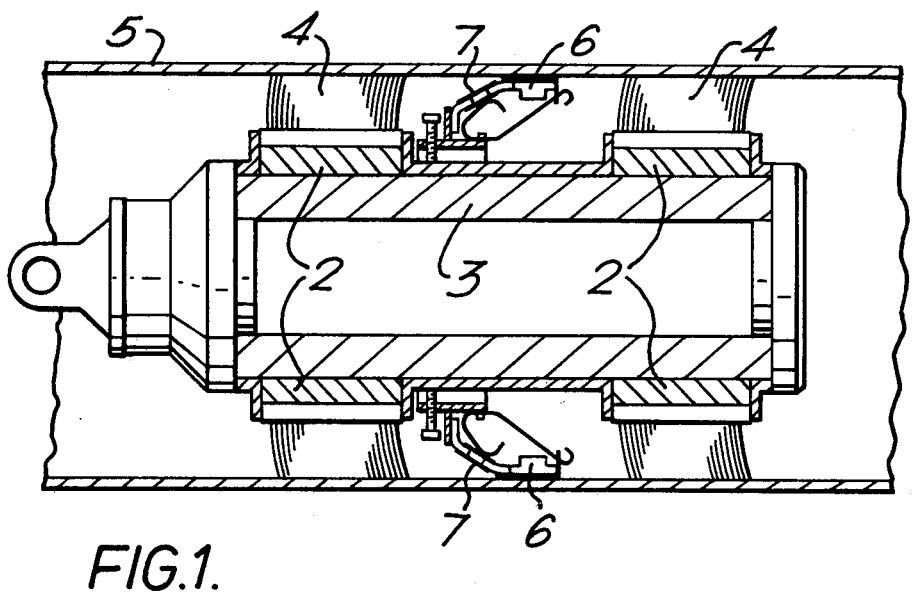

United States Patent [19]

Sharp et al.

[11] 4,447,777
[45] May 8, 1984

[54] MAGNETIC PIPELINE INSPECTION VEHICLE WITH METALLIC FOIL AND BRISTLE CONTACTS SUPPORTING THE VEHICLE

[75] Inventors: Michael R. G. Sharp, Whitley Bay; John C. Braithwaite, Ponteland, both of England

[73] Assignee: British Gas Corporation, London, England

[21] Appl. No.: 216,499

[22] Filed: Dec. 15, 1980

[30] Foreign Application Priority Data

Oct. 17, 1980 [GB] United Kingdom ................ 8033618

[51] Int. Cl.³ ..................... G01N 27/72; G01N 27/82
[52] U.S. Cl. ................................................ 324/220
[58] Field of Search ................................ 324/219–221

[56] References Cited

U.S. PATENT DOCUMENTS 3,593,122  7/1971  Barton et al. ...................... 324/220
4,310,396  1/1982  Braithwaite et al. ............... 324/220

*Primary Examiner*—Gerard R. Strecker
*Assistant Examiner*—Walter E. Snow
*Attorney, Agent, or Firm*—Lalos, Leeds, Keegan, Lett & Marsh

[57] ABSTRACT

An improved magnet assembly for a magnetic pipeline inspection vehicle in which the assembly is rigidly secured on the body of the vehicle which is ferromagnetic and provides an annular magnetic return path between magnetic pole members formed of permanent magnets and flexible bristles or foils.

26 Claims, 5 Drawing Figures

MAGNETIC PIPELINE INSPECTION VEHICLE WITH METALLIC FOIL AND BRISTLE CONTACTS SUPPORTING THE VEHICLE

This invention relates to pipeline vehicles intended for the detection of defects in the walls of pipeline constructed of ferromagnetic material when traversing the inside of the pipeline, and in particular to magnet assemblies for such vehicles.

A complete pipeline inspection vehicle normally consists of several elements or modules flexibly linked together by towing couplings and operating as a single train.

Usually, pipeline inspection vehicles of the kind with which the present invention is particularly concerned operate by permeating an area of the pipe wall with magnetic flux from spaced arrays of magnets of a magnet assembly resiliently mounted on one of the vehicle modules and detecting anomalies in the magnetic field adjacent to the pipe wall caused by flux leakage around defects.

The motive power for pipeline vehicles is normally provided by fitting cup rubbers to one or more modules of the vehicle train. These cup rubbers fit closely against the pipe wall, creating a fluid tight seal, and ensure that the vehicle train is driven forward by the flow of liquid or gas in the pipeline.

These drive cup rubbers may be mounted in the module containing the magnet assemblies with certain advantages hereinafter described, or on a separate 'traction' module. At least two drive cup rubbers are normally provided, to provide continuity of driving impulse when one cup rubber is abreast of a branch pipe or other discontinuity in the pipe wall profile.

At least one of the drive cup rubbers is normally mounted on the leading module of the train. The second drive cup rubber may also be mounted on this module, spaced axially from it by at least one pipe diameter, or mounted on the second or subsequent module.

It will be apparent therefore, that the magnet assembly module, with which this invention is particularly concerned, may be the leading element in a multi-module train, if it is fitted with a drive cup, or it may operate behind a separate traction module.

The space available for a magnet assembly is limited and requires magnet assemblies of compact size and high ratios of magnetic field to magnet volume. Suitable magnet designs are described in our British patent specification No. 1,510,225.

The coupling member that couples each magnet to the pipe wall has a major effect on the performance of the magnet system. The requirements are that it should wear well, and that the magnetic reluctance should be low, and should not vary significantly when traversing obstructions or welds and it should not induce excessive drag or resistance to motion of the pipeline vehicle. These functions may be fulfilled by coupling members constructed of wire bristles or metal foils as described in U.S. Pat. No. 4,310,796, or with a mixture of wire bristles or metal foils of the kind disclosed therein.

A difficulty arises in the design of magnetic pipeline inspection vehicles in that pipelines are normally constructed by welding together lengths of pipe of uniform external diameter. Changes in pipeline wall thickness therefore give rise to variations in the diameter of the internal bore of pipelines. Such wall thickness variations are commonly used to reduce the stress levels in the pipe in urban areas, or to provide reinforcement at road crossings and the like and at pipe bends and off-take points.

Variations in pipeline bore can naturally give rise to unsteady running in gas driven pipeline vehicles unless special means are adopted to mitigate the effect of bore variation. One such means is to resiliently mount the magnet assemblies on springs carried by the vehicle body so that each magnet assembly consisting of magnets, coupling member, and flux return path member, is pressed into engagement with the pipe wall. Such an arrangement is more completely described in our said U.S. Pat. No. 4,310,796.

Such an arrangement works reasonably well but has the disadvantage that the relatively large mass of the spring-supported magnet assembly has a high inertia and induces large shock loads in the pipeline vehicle when a step in the pipe bore is encountered, particularly if the vehicle is moving rapidly. The disadvantages of large unsprung weights on vehicle suspension is well known, in relation to wheeled vehicles. Substantially similar considerations arise in pipeline vehicles with heavy magnet assemblies supported on bristles or foils.

An object of the present invention is to provide a magnetic pipeline inspection vehicle, and magnet assemblies for such vehicles, less subject to the aforesaid disadvantages.

According to the present invention, in a magnetic pipeline inspection vehicle having a magnet assembly which includes magnets fitted on a flux-return-path member, and magnetic coupling members attached to said magnets and arranged to engage the surface of the pipeline so as to couple the magnetic flux with the wall of the pipeline, the return-path member is an annular member forming a rigid part of the vehicle body, and said magnets and coupling members are rigidly but detachably secured to the annular member, coupling members also provide at least part of the means for supporting the vehicle in the pipeline and for maintaining magnetic coupling over regions of changes in pipeline geometry, the nature and/or the stiffness of the coupling members being carefully optimised to give the lowest acceptable levels of;

(a) magnetic reluctance between the coupling members and the pipeline wall, (b) resistance to motion of the vehicle through the pipeline, and (c) abrasive wear of the coupling members.

It has, however, been found that, provided the stiffness of the magnetic coupling element (i.e. either the aforesaid bristles or foils) is carefully optimised and made not greater than that necessary to support the vehicle weight, the vehicle has a lower bore-dependent drag or resistance to motion than an equivalent vehicle with articulating magnet assemblies of equivalent performance.

A further alternative in accordance with the invention, which allows the magnetic inspection vehicle to be the leading element in a multi-vehicle train, is to fit flexible cup-shaped sealing members to the vehicle. As described, these cup members are normally used on pipeline vehicles or vehicle trains to provide the traction element in the train. When fitted to the magnetic inspection vehicle of annular construction, they also provide an element of radial support to supplement that provided by the bristles or foils.

There is an advantage in mounting the drive-producing element on the same module as the drag-inducing element in that, if they are mounted on separate modules, the drag produces high towing forces in the coupling linking the modules, and when the separate vehicle elements are traversing a pipe bend, the towing load has a sideways component which induces additional friction between the vehicles and the pipe which contributes to unsteady running. Mounting the drive cup rubbers on the magnetic inspection module avoids this problem to a large degree.

The individual bristle or foil elements are the only element that responds to bore variations or steps. These have low mass. Hence the disadvantage of the high unsprung weight associated with articulating magnet assemblies is avoided without any penalty in respect of bore-dependent drag.

Alternatively, in accordance with the invention, the magnetic coupling element may be made even less stiff to optimise the magnetic and low drag characteristics above, the weight of the vehicle being carried mainly by wheels attached to the vehicle running along the inside wall of the pipe.

A further alternative in accordance with the invention, is to use a mixture of stiff and flexible bristles or foils to carry the weight of the vehicle and to maintain magnetic coupling over regions of changes in pipeline geometry, e.g. pipe ovality or bends.

A further alternative in accordance with the invention, which allows the magnetic inspection vehicle to be the leading element in a multi-vehicle train, is to fit flexible cup-shaped sealing members to the vehicle. These cup members are normally used on pipeline vehicles or vehicle trains to provide the traction element in the train in that they fit closely against the pipe wall and create a seal with the wall surface to ensure that the vehicles are driven forward by the flow of gas or liquid in the pipeline. When fitted to a magnetic inspection vehicle of annular construction, they also provide an element of radial support to supplement that provided by the bristles or foils.

Figure 2:
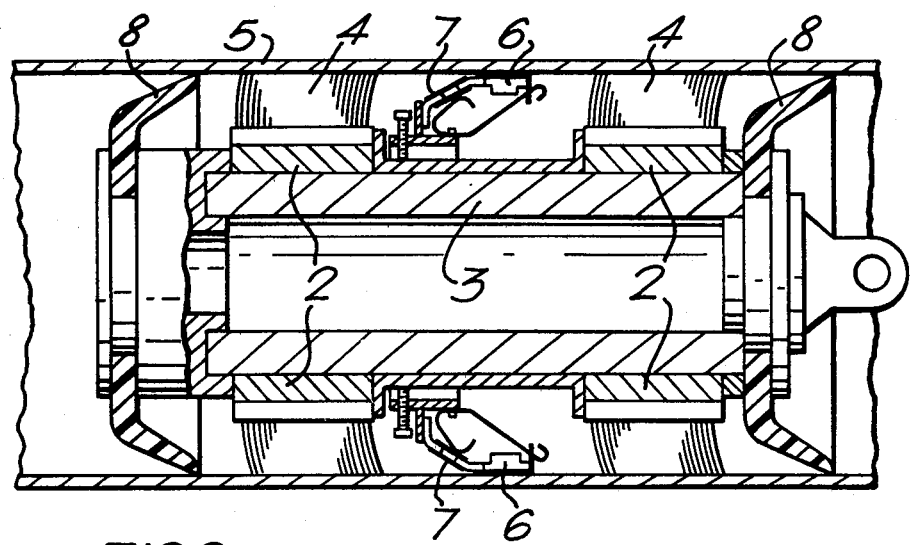
Figure 3:
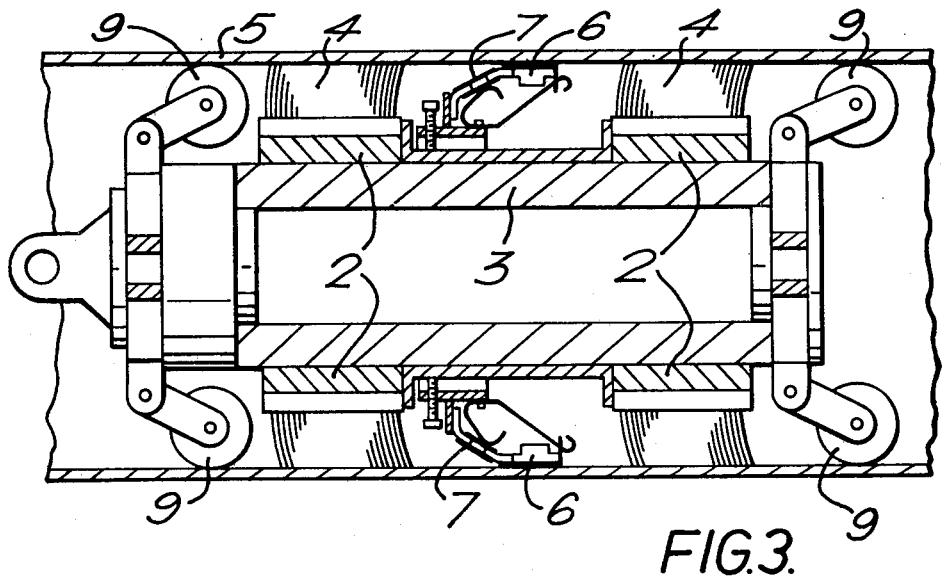
Figure 4:
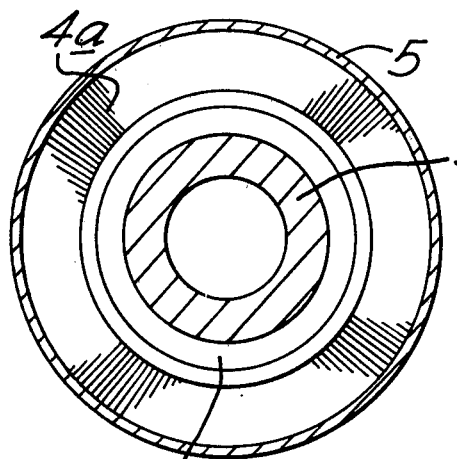
Figure 5:
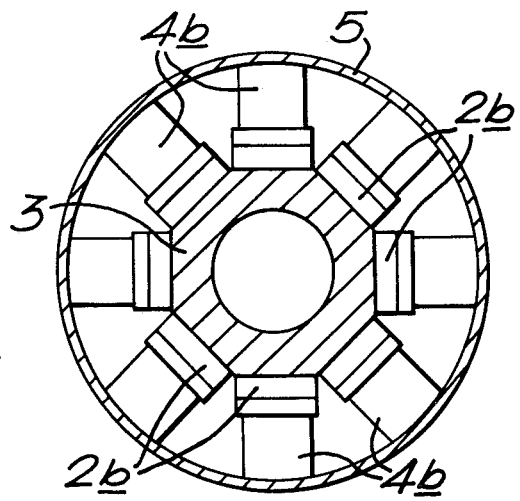

Embodiments of the invention will now be described, by way of example, with reference to the accompanying drawings in which:

FIG. 1 is a diagrammatic longitudinal sectional elevation of a magnetic pipeline inspection vehicle showing one embodiment, FIG. 2 is a view similar to FIG. 1 showing another embodiment, FIG. 3 is a view similar to FIG. 1 showing yet another embodiment, and FIGS. 4 and 5 are diagrammatic cross-sectional end views of any one of the embodiments shown in FIGS. 1, 2 or 3 showing alternative forms of construction of the magnets, magnetic coupling elements, and magnetic flux return path member.

Referring first to FIG. 1, the magnet assembly for this particular form of magnetic pipeline inspection vehicle comprises an arrangement of permanent magnets 2 of opposite polarity fitted, respectively, at each end of an annular ferro-magnetic flux return path body 3 of the magnetic circuit. A flux coupling assembly 4 consisting either of ferro-magnetic bristles or foils (as described in said U.S. Pat. No. 4,310,796) is mounted externally to each magnet 2 and bridges the annular gap between the magnets and the wall of the ferro-magnetic pipeline 5 whereby to induce a relatively strong magnetic field in that region of the pipeline wall under examination. The magnetic lines of force are constrained within that region, but where a fault or defect occurs there is a higher leakage field which is detected by sensors in a plurality of detector modules 6 which are carried by sledge units 7.

The bristles (or foils) are manufactured so that the external diameter of the coupling assembly is greater than the maximum pipe bore to be encountered. The bristles accordingly are deflected (as shown) towards the rear of the inspection vehicle when the vehicle is moving forward in the pipeline.

The bristles (or foils) of the coupling assembly 4 are proportioned to be as long as possible in the radial direction, consistent with the provision of magnets and magnetic return path of adequate strength and cross-section. The total bristle (or foil) stiffness in this example should be adequate to support the weight of the inspection vehicle and adequately control its attitude when traversing bends, but the assembly should have sufficient flexibility to give a small variation in drag when moving in the axial direction through pipelines of varying wall thickness.

Referring to the embodiment shown in FIG. 2, this magnetic pipeline inspection vehicle is also equipped to allow it to be the leading element in a multi-vehicle train and for this purpose is provided with flexible cup-shaped discs 8 which provide a seal with the pipeline wall enabling the vehicle to be driven forward by the flow of fluid in the pipeline. Conveniently, in this case, the discs 8 also provide an element of radial support for the weight of the vehicle to supplement that provided by the bristles or foils 4 which can then be relatively less stiff than in the first example whereby to optimise the magnetic coupling characteristics.

Referring to FIG. 3, the bristles or foils can again be relatively less stiff than in the first example, and the weight of the vehicle shared by them and a plurality of spring-loaded wheels 9 which are attached to the vehicle and run along the inside wall of the pipeline.

In all the aforesaid embodiments, the arrangement of magnets 2 and bristle or foil magnetic coupling assemblies 4 may be in the form of construction shown in either FIG. 4 or FIG. 5. In FIG. 4, the magnets 2a and coupling assemblies 4a are of annular form rigidly mounted on the flux return path body 3, whereas in FIG. 5 a plurality of magnets 2b and coupling assemblies 4b are rigidly mounted on facets of the flux return path body 3 extending radially outwardly therefrom.

We claim:

1. A magnetic pipeline inspection vehicle comprising:
    a vehicle body comprising a rigid, elongated, annular, magnetic flux-return-path member;
    permanent magnet means mounted rigidly and directly on the outer surface of the annular member and in magnetic flux conducting relationship thereto; and
    magnetic coupling means mounted directly on said magnet means and in magnetic flux conducting relationship thereto, said coupling means being positioned so as to engage the inner surface of a pipeline being inspected when the vehicle is in the pipeline to thereby couple the magnet means and the pipeline in magnetic flux conducting relationship and provide support for the vehicle as it travels in the pipeline.

2. An inspection vehicle as set forth in claim 1 wherein said coupling means comprises a plurality of generally radially extending, metallic, flexible, resilient wire bristle elements.

3. An inspection vehicle as set forth in claim 1 wherein said coupling means comprises a plurality of generally radially extending, metallic, flexible, resilient foil elements.

4. An inspection vehicle as set forth in claim 1 wherein said coupling means comprises a mixture of generally radially extending, metallic, flexible, resilient wire bristle elements and foil elements.

5. An inspection vehicle as set forth in claim 2 wherein the initial unflexed external diameter of the coupling means is greater than the maximum pipeline bore expected to be encountered, and bristle elements of said coupling means being deflected towards the rear of the vehicle as the latter is inserted into and moves forwardly in the pipeline.

6. An inspection vehicle as set forth in claim 3 wherein the initial unflexed external diameter of the coupling means is greater than the maximum pipeline bore expected to be encountered, the foil elements of said coupling means being deflected towards the rear of the vehicle as the latter is inserted into and moves forwardly in the pipeline.

7. An inspection vehicle as set forth in claim 4 wherein the initial unflexed external diameter of the coupling means is greater than the maximum pipeline bore expected to be encountered, the elements of said coupling means being deflected towards the rear of the vehicle as the latter is inserted into and moves forwardly in the pipeline.

8. An inspection vehicle as set forth in claim 1 wherein the magnetic coupling means supports the entire weight of the vehicle as it travels in the pipeline.

9. An inspection vehicle as set forth in claim 1 and further comprising a plurality of articulating wheels mounted on the vehicle body in a position for running along the inside wall of the pipeline and supporting a portion of the weight of the vehicle as it travels in the pipeline.

10. An inspection vehicle as set forth in claim 1 and further comprising at least two flexible cup-shaped drive members mounted in longitudinally spaced relationship on the body in a position for sealingly contacting the inner wall of the pipeline to enable the vehicle to be driven through the pipeline by flow of fluid in the latter, said drive members supporting a portion of the weight of the vehicle as it travels in the pipeline.

11. An inspection vehicle as set forth in claim 1 wherein the permanent magnet means comprises a pair of annular magnets of opposite polarity disposed in longitudinally spaced relationship on the body.

12. An inspection vehicle as set forth in claim 11 wherein the coupling means comprises a respective annular array of radially extending coupling elements for each magnet.

13. An inspection vehicle as set forth in claim 1 wherein the coupling means comprises an annular array of radially extending coupling elements.

14. An inspection vehicle as set forth in claim 1 wherein the magnet means and the coupling means are each of annular form.

15. An inspection vehicle as set forth in claim 2 wherein the permanent magnet means comprises a pair of annular magnets of opposite polarity disposed in longitudinally spaced relationship on the body.

16. An inspection vehicle as set forth in claim 15 wherein the coupling means comprises a respective annular array of said bristle elements for each magnet.

17. An inspection vehicle as set forth in claim 2 wherein the coupling means comprises an annular array of said bristle elements.

18. An inspection vehicle as set forth in claim 3 wherein the permanent magnet means comprises a pair of annular magnets of opposite polarity disposed on the body in longitudinally spaced relationship.

19. An inspection vehicle as set forth in claim 18 wherein the coupling means comprises a respective annular array of said foil elements for each magnet.

20. An inspection vehicle as set forth in claim 3 wherein the coupling means comprises an annular array of said foil elements.

21. An inspection vehicle as set forth in claim 1 wherein said permanent magnet means comprises first and second sets of individual magnets, the respective magnets of each set being spaced circumferentially on the body, said sets being of respective opposite polarities and being disposed on the body in longitudinally spaced relationship.

22. An inspection vehicle as set forth in claim 21 wherein the coupling means comprises a respective set of coupling elements for each magnet.

23. An inspection vehicle as set forth in claim 2 wherein said permanent magnet means comprises first and second sets of individual magnets, the respective magnets of each set being spaced circumferentially on the body, said sets being of respective opposite polarities and being disposed on the body in longitudinally spaced relationship.

24. An inspection vehicle as set forth in claim 23 wherein the coupling means comprises a respective set of said bristle elements for each magnet.

25. An inspection vehicle as set forth in claim 3 wherein said permanent magnet means comprises first and second sets of individual magnets, the respective magnets of each set being spaced circumferentially on the body, said sets being of respective opposite polarities and being disposed on the body in longitudinally spaced relationship.

26. An inspection vehicle as set forth in claim 25 wherein the coupling means comprises a respective set of said foil elements for each magnet.

* * * * *